(12) United States Patent
Shirota et al.

(10) Patent No.: US 11,064,962 B2
(45) Date of Patent: Jul. 20, 2021

(54) X-RAY IMAGING APPARATUS

(71) Applicant: Shimadzu Corporation, Kyoto (JP)

(72) Inventors: Ken Shirota, Kyoto (JP); Junpei Sakaguchi, Kyoto (JP); Hiroshi Okumura, Kyoto (JP)

(73) Assignee: Shimadzu Corporation, Kyoto (JP)

(*) Notice: Subject to any disclaimer, the term of this patent is extended or adjusted under 35 U.S.C. 154(b) by 38 days.

(21) Appl. No.: 16/681,162

(22) Filed: Nov. 12, 2019

(65) Prior Publication Data

US 2020/0214656 A1 Jul. 9, 2020

(30) Foreign Application Priority Data

Jan. 8, 2019 (JP) .............................. JP2019-001422

(51) Int. Cl.
*A61B 6/00* (2006.01)

(52) U.S. Cl.
CPC .......... *A61B 6/4482* (2013.01); *A61B 6/4452* (2013.01); *A61B 6/467* (2013.01); *A61B 6/545* (2013.01); *A61B 6/4464* (2013.01)

(58) Field of Classification Search
CPC ..... A61B 6/4452; A61B 6/4464; A61B 6/545; A61B 6/467; A61B 6/4482; A61B 6/105; A61B 17/1626; A61B 17/1628
See application file for complete search history.

(56) References Cited

U.S. PATENT DOCUMENTS

| 8,755,492 B2 * | 6/2014 | Lee ...................... A61B 6/4476 378/115 |
| 2019/0239835 A1 * | 8/2019 | Okuno ................... A61B 6/105 |

FOREIGN PATENT DOCUMENTS

JP 2010-227376 A 10/2010

OTHER PUBLICATIONS

Product information from a website of Canon Medical Systems Corporation. Available at https://jp.medical.canon/products/xray/radrex_drite (this or similar version appears to have been listed Cannon website at least on Sep. 21, 2018.).

* cited by examiner

*Primary Examiner* — Don K Wong
(74) *Attorney, Agent, or Firm* — Muir Patent Law, PLLC

(57) ABSTRACT

An X-ray imaging apparatus includes an X-ray tube, an X-ray detector, a moving body movable in a predetermined direction, a moving mechanism, a motor, an operating force detector configured to detect an operating force, and a controller configured or programmed to perform mode switching control to switch, based on whether or not an operation to enable manual movement of the moving body has been detected, a control mode to a torque control mode or a position control mode.

7 Claims, 5 Drawing Sheets

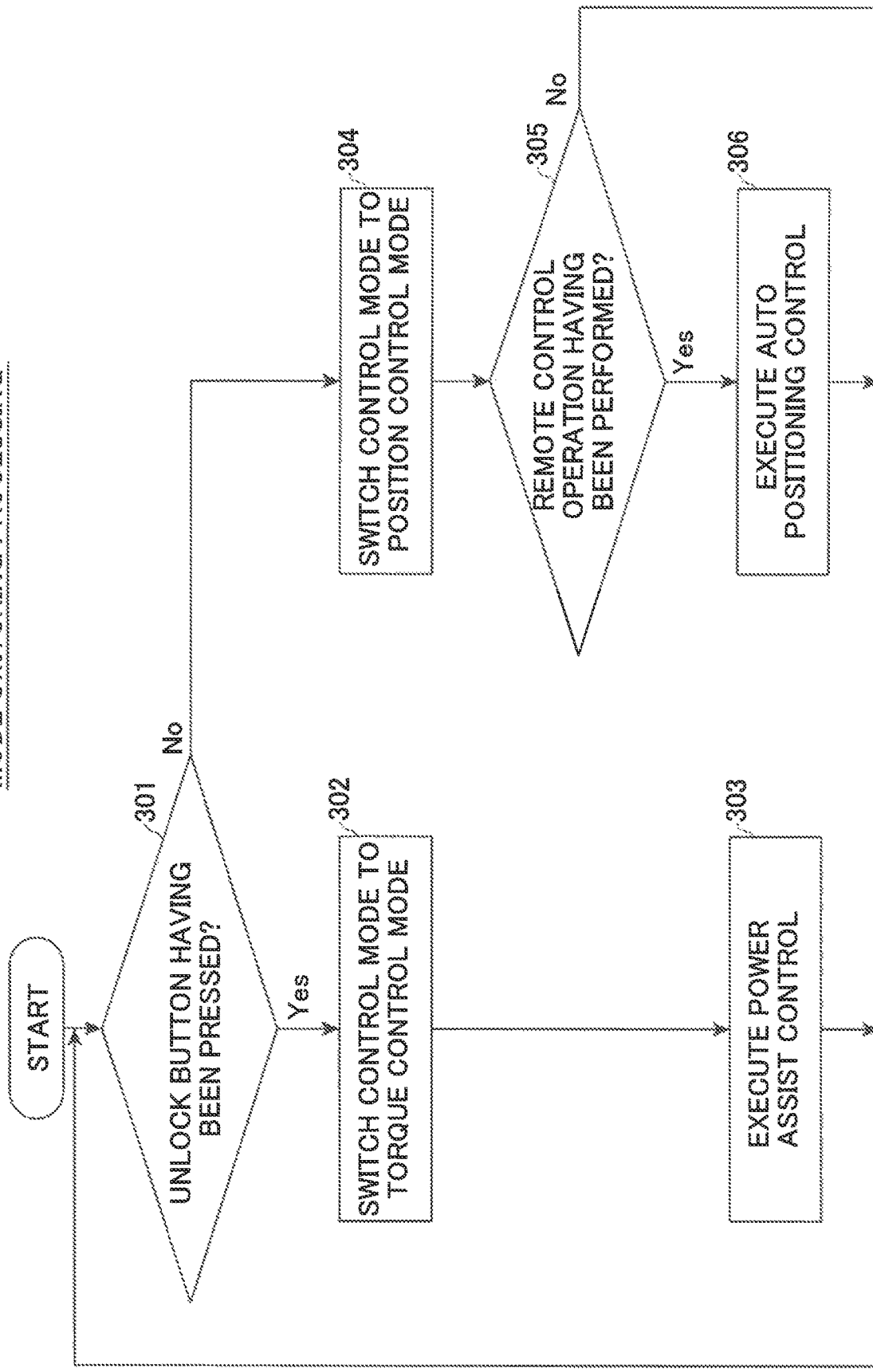

X-RAY IMAGING APPARATUS

CROSS-REFERENCE TO RELATED APPLICATIONS

This application claims the benefit of priority to Japanese Patent Application No. 2019-001422 filed on Jan. 8, 2019, the entire contents of this application being hereby incorporated herein by reference.

BACKGROUND OF THE INVENTION

Field of the Invention

The present invention relates to an X-ray imaging apparatus.

Description of the Background Art

Conventionally, an X-ray imaging apparatus is known. Such an X-ray imaging apparatus is disclosed in Japanese Patent Laid-Open No. 2010-227376, for example.

Japanese Patent Laid-Open No. 2010-227376 discloses an X-ray imaging apparatus including a radiation source, radiation detection means, an operation unit that detects a force for manually moving the radiation source, a servomotor that moves the radiation source, and a controller that controls the servomotor. In the X-ray imaging apparatus described in Japanese Patent Laid-Open No. 2010-227376, the controller is configured or programmed to control the servomotor in accordance with the force for manually moving the radiation source so as to perform operation assist (power assist) when the radiation source is manually moved. In this operation assist (power assist), the controller performs position control in which control based on the position and speed is performed.

Although not clearly described in Japanese Patent Laid-Open No. 2010-227376, auto positioning control in which the radiation source automatically moves based on the current position and the registered movement target position of the radiation source requires high-precision positioning, and thus the position control in which the target position and the speed to reach the target position are controlled is essential. In other words, it is conventionally known to perform the position control in which control based on the position and speed is performed also in the auto positioning control similarly to the operation assist (power assist) described in Japanese Patent Laid-Open No. 2010-227376.

As described above, conventionally, it is possible to accurately move the radiation source by performing the auto positioning control by the position control in which control based on the position and speed is performed. However, in the X-ray imaging apparatus described in Japanese Patent Laid-Open No. 2010-227376, even when the radiation source is manually moved, the controller performs the position control in which control based on the position and speed is performed in accordance with the force for manually moving the radiation source to provide power assist. Thus, when the radiation source is manually moved, an operating force for manually moving the radiation source is converted into a speed and assisted, and thus the operating force is assisted by an indirect speed rather than a direct force. Therefore, an operator disadvantageously feels strange when performing an operation. Consequently, the operability is decreased when the operator manually moves the radiation source.

SUMMARY OF THE INVENTION

The present invention is intended to solve the above problem. The present invention aims to provide an X-ray imaging apparatus capable of accurately moving at least one of an X-ray tube and an X-ray detector when at least one of the X-ray tube and the X-ray detector is automatically moved, and capable of significantly reducing or preventing a decrease in operability when at least one of the X-ray tube and the X-ray detector is manually moved.

An X-ray imaging apparatus according to an aspect of the present invention includes an X-ray tube configured to irradiate a subject with X-rays, an X-ray detector configured to detect the X-rays transmitted through the subject, a moving body including at least one of the X-ray tube and the X-ray detector, the moving body being movable in a predetermined direction, a moving mechanism configured to support the moving body in such a manner that the moving body is movable in the predetermined direction, a motor provided in the moving mechanism, an operating force detector configured to detect an operating force applied to move the moving body, and a controller configured or programmed to perform mode switching control to switch, based on whether or not an operation to enable manual movement of the moving body has been detected, a control mode to a torque control mode in which a torque of the motor is controlled so as to change an amount of assist to be provided to the moving body when the moving body is manually moved, or a position control mode in which the motor is controlled to move the moving body based on a current position and a movement target position of the moving body.

The X-ray imaging apparatus according to this aspect of the present invention includes the controller configured or programmed to perform the mode switching control to switch, based on whether or not the operation to enable the manual movement of the moving body has been detected, the control mode to the torque control mode in which the torque of the motor is controlled so as to change the amount of assist to be provided to the moving body when the moving body is manually moved, or the position control mode in which the motor is controlled based on the current position and the movement target position of the moving body to move the moving body. Accordingly, when at least one of the X-ray tube and the X-ray detector is manually moved, the control mode is switched to the torque control mode to control the generated torque of the motor such that the operating force applied to move the moving body can be assisted by controlling the torque (drive force) of the motor. Therefore, the operating force is assisted by a direct force (torque), and thus it is possible to perform good power assist with no sense of strangeness. Consequently, it is possible to significantly reduce or prevent a decrease in operability when at least one of the X-ray tube and the X-ray detector is manually moved. Furthermore, it is possible to switch the control mode to the position control mode in which high-precision position control is possible at the time of auto positioning control in which the moving body is automatically moved based on the current position and the registered movement target position of the moving body. Consequently, at the time of the auto positioning control, the high-precision position control can be performed. Thus, it is possible to accurately move at least one of the X-ray tube and the X-ray detector when at least one of the X-ray tube and the X-ray detector is automatically moved, and it is possible to significantly reduce or prevent a decrease in operability when at least one of the X-ray tube and the X-ray detector is manually moved. Moreover, the controller performs the mode switching control based on whether or not the operation to enable the manual movement of the moving body has been detected, and thus the controller performs the mode switching control depending on whether or not an operator has performed the operation to enable the manual movement of the moving body. Thus, when the operator manually moves the moving body, the control mode can be reliably switched to the torque control mode. Consequently, the control mode can be easily switched.

The X-ray imaging apparatus according to this aspect of the present invention further includes a movement availability switch configured to switch between a state in which movement of the moving body is permitted in the predetermined direction and a state in which the movement is prohibited in the predetermined direction, and the controller is preferably configured or programmed to perform the mode switching control based on detection of a switching operation of the movement availability switch as whether or not the operation to enable the manual movement of the moving body has been detected. Accordingly, an operation of switching to a state in which the movement is permitted is performed such that the control mode can also be switched to the torque control mode. Furthermore, an operation of switching to a state in which the movement is prohibited is performed such that the control mode can also be switched to the position control mode. Consequently, it is possible to significantly reduce or prevent an increase in imaging procedures (the workload on the operator) as compared with the case in which an operation for switching the control mode is performed separately.

In this case, the X-ray imaging apparatus preferably further includes a grip provided on the moving body and held when the moving body is manually moved, and a plurality of buttons provided in a vicinity of the grip, and the controller is preferably configured or programmed to switch the movement availability switch and perform the mode switching control to switch the control mode to the torque control mode when at least one of the plurality of buttons is pressed, and to switch the movement availability switch and perform the mode switching control to switch the control mode to the position control mode when at least one of the plurality of buttons that has been pressed is released. Accordingly, as compared with the case in which a separate button is provided to switch the control mode, it is possible to significantly reduce or prevent an increase in the number of components and to significantly reduce or prevent the complicated apparatus configuration.

In the X-ray imaging apparatus according to this aspect of the present invention, the controller is preferably configured or programmed to perform the mode switching control based on whether or not the operating force detector has detected the operating force as whether or not the operation to enable the manual movement of the moving body has been detected. Accordingly, the control mode can be switched simply by manually moving the moving body, and thus unlike the case in which a separate button is provided to switch the control mode, it is possible to significantly reduce or prevent an increase in the number of components and to significantly reduce or prevent the complicated apparatus configuration.

In the X-ray imaging apparatus according to this aspect of the present invention, the moving mechanism preferably includes a guide including a plurality of rails, and a moving body support configured to support the moving body in such a manner that the moving body is movable in a vertical direction and a horizontal direction along the guide, and the controller is preferably configured or programmed to control the torque of the motor so as to change the amount of assist to be provided to the moving body, and move the moving body support in the vertical direction and the horizontal direction in the torque control mode, and to control the motor based on the current position and the movement target position of the moving body to move the moving body in the vertical direction and the horizontal direction, and move the moving body support in the position control mode. Accordingly, the moving body support supporting the moving body moves along the rails of the guide, and thus the moving body and the moving body support can be stably moved. Furthermore, even when the moving body and the moving body support are heavy, the moving body and the moving body support can be moved along the rails of the guide, and thus the moving body and the moving body support can be easily moved when the moving body is manually moved.

The X-ray imaging apparatus according to this aspect of the present invention preferably further includes an input device through which an operation related to movement of the moving body is performed, and the controller is preferably configured or programmed to perform auto positioning control to automatically move the moving body to a registered position based on the operation through the input device in the position control mode. Accordingly, the auto positioning control can be performed in a state in which the control mode is switched to the position control mode in which the high-precision position control is possible, and thus the operator can easily and accurately move the moving body to the target position.

In the X-ray imaging apparatus according to this aspect of the present invention, the motor preferably includes a servomotor configured to switch between the torque control mode in which the torque of the motor is controlled so as to change the amount of assist to be provided to the moving body and the position control mode in which the motor is controlled based on the current position and the movement target position of the moving body to move the moving body, and the controller is preferably configured or programmed to switch the motor to the torque control mode or the position control mode based on whether or not the operation to enable the manual movement of the moving body has been detected. Accordingly, the torque control mode and the position control mode can be driven by the common motor, and thus as compared with the case in which the motor is provided separately for each of the torque control mode and the position control mode, it is possible to significantly reduce or prevent an increase in the number of components and to significantly reduce or prevent the complicated apparatus configuration.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 6 is a flowchart for illustrating mode switching processing performed by the controller of the X-ray imaging apparatus according to the embodiment of the present invention.

DESCRIPTION OF THE PREFERRED EMBODIMENTS

An embodiment of the present invention is hereinafter described with reference to the drawings.

(Configuration of X-Ray Imaging Apparatus)

The overall configuration of an X-ray imaging apparatus 100 according to the embodiment of the present invention is now described with reference to FIG. 1.

Figure 1:
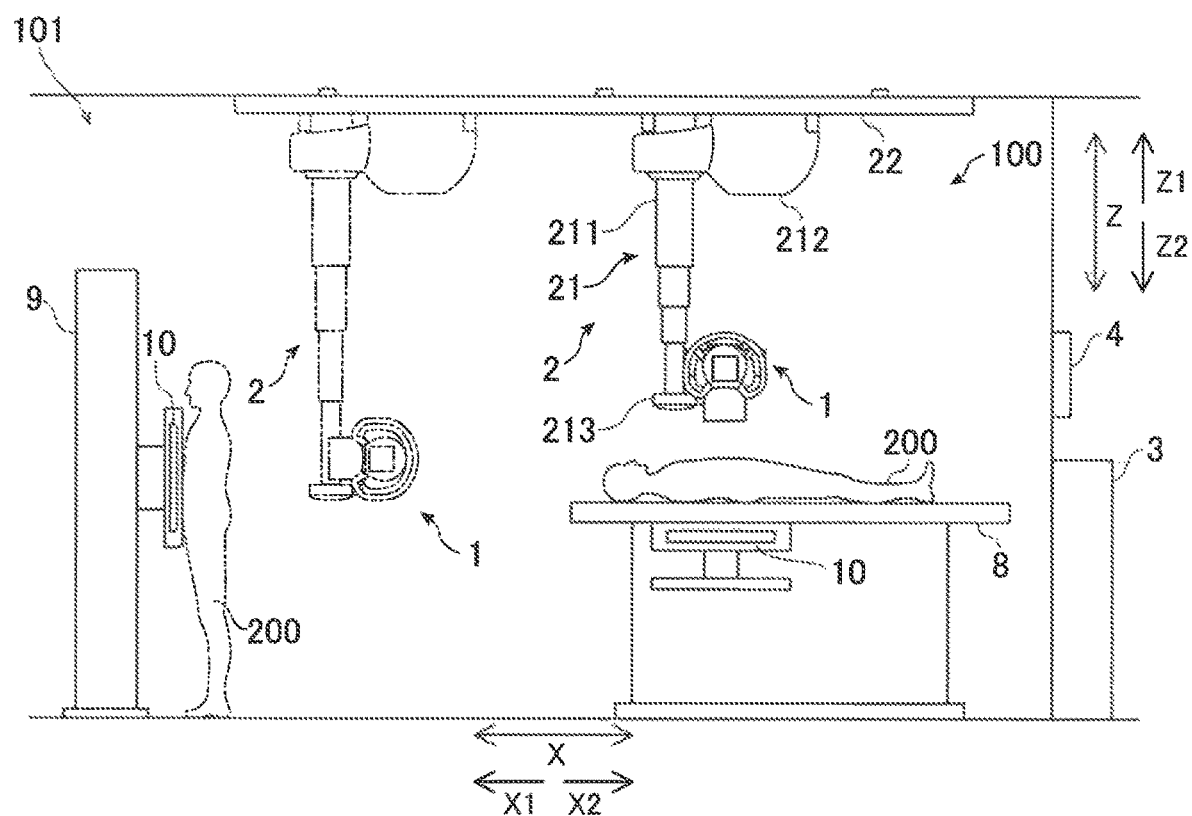
FIG. 1 is a schematic view showing the overall configuration of an X-ray imaging apparatus according to an embodiment of the present invention.

FIG. 1 shows an example of a ceiling-suspended X-ray imaging apparatus 100 installed in an imaging room 101. The X-ray imaging apparatus 100 mainly includes a moving body 1, a moving mechanism 2, a controller 3, a remote control 4, and X-ray detectors 10. The remote control 4 is an example of an "input device" in the claims.

In the ceiling-suspended X-ray imaging apparatus 100, the moving body 1 including an X-ray tube 11 is supported by the moving mechanism 2 so as to be suspended from the ceiling. The moving body 1 is supported by the moving mechanism 2 in such a manner as to be movable in the imaging room 101.

The X-ray imaging apparatus 100 is a medical X-ray imaging apparatus, and is configured to radiograph a subject 200 to be imaged. The X-ray imaging apparatus 100 includes an imaging table 8 to image the lying subject 200 (in the recumbent position), and an imaging stand 9 to image the standing subject 200 (in the upright position). The X-ray detectors 10 are movably held by the imaging table 8 and the imaging stand 9, respectively. The X-ray detectors 10 are flat panel detectors (FPDs), for example, and are configured to detect X-rays transmitted through the subject 200. A guide 22 can move the moving body 1 at least between a position at which imaging in the recumbent position using the imaging table 8 is performed (see solid lines in FIG. 1) and a position at which imaging in the upright position using the imaging stand 9 is performed (see two-dot chain lines in FIG. 1).

In imaging in the recumbent position, the moving body 1 is disposed at a position that faces the X-ray detector 10 of the imaging table 8 in a vertical direction, and the subject 200 lying on the imaging table 8 is imaged between the X-ray tube 11 and the X-ray detector 10 that face each other in the vertical direction. In imaging in the upright position, the moving body 1 is disposed at a position that faces the X-ray detector 10 of the imaging stand 9 in a horizontal direction, and the subject 200 standing in front of the imaging stand 9 is imaged between the X-ray tube 11 and the X-ray detector 10 that face each other in the horizontal direction. Furthermore, in the X-ray imaging apparatus 100, general imaging (imaging in which the posture is not specified) in which the subject 200 in an arbitrary posture can be imaged from an arbitrary direction can be performed by disposing a portable X-ray detector 10 at an arbitrary position in the imaging room 101, and moving the moving body 1 to a position that faces the X-ray detector 10.

The X-ray imaging apparatus 100 also includes the controller 3 and the remote control 4. The controller 3 includes a central processing unit (CPU) and a memory. The controller 3 controls X-ray imaging with the X-ray tube 11 and the X-ray detectors 10, controls movement of the moving body 1, and control switching (movement availability switching control and mode switching control). The remote control 4 is provided to perform an operation related to movement of the moving body 1. The remote control 4 has a function of receiving an input operation related to X-ray imaging. The input operation includes auto positioning control, setting of imaging conditions for X-ray imaging, an instruction to start X-ray irradiation, etc.

(Moving Body)

Figure 2:
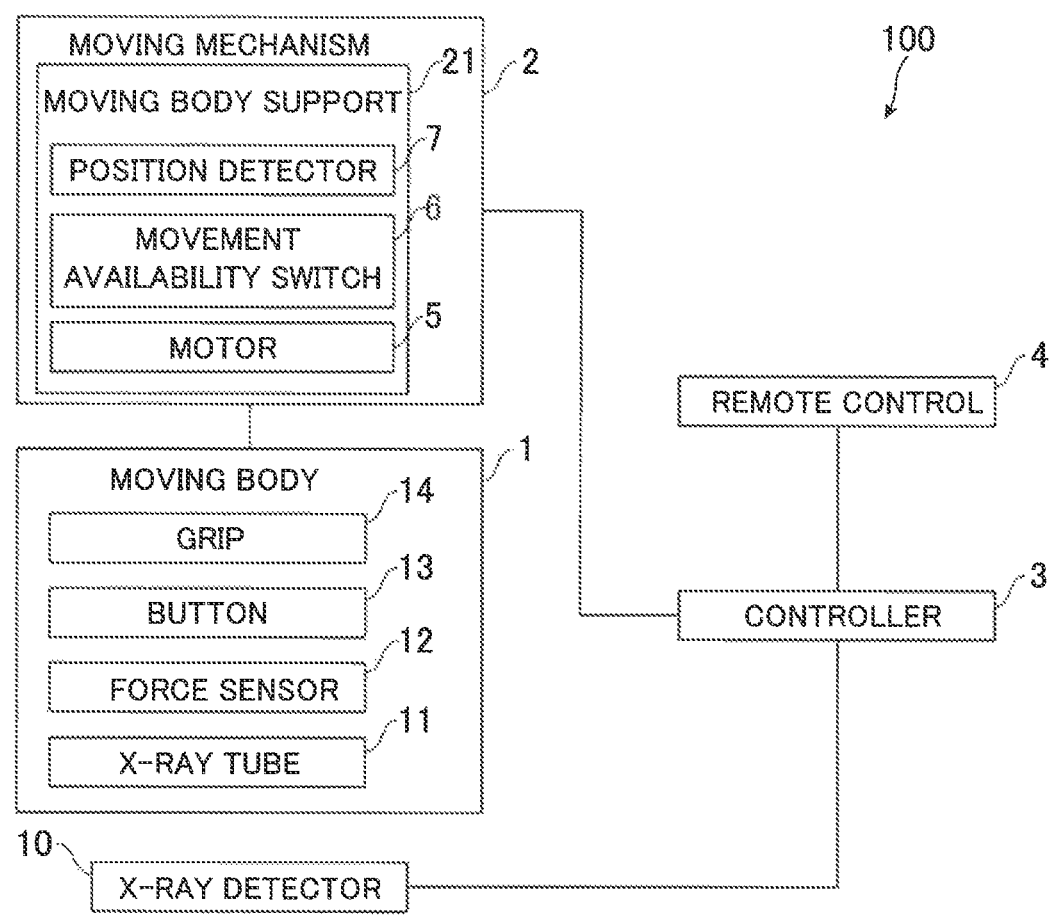
FIG. 2 is a block diagram showing the overall configuration of the X-ray imaging apparatus according to the embodiment of the present invention.
Figure 3:
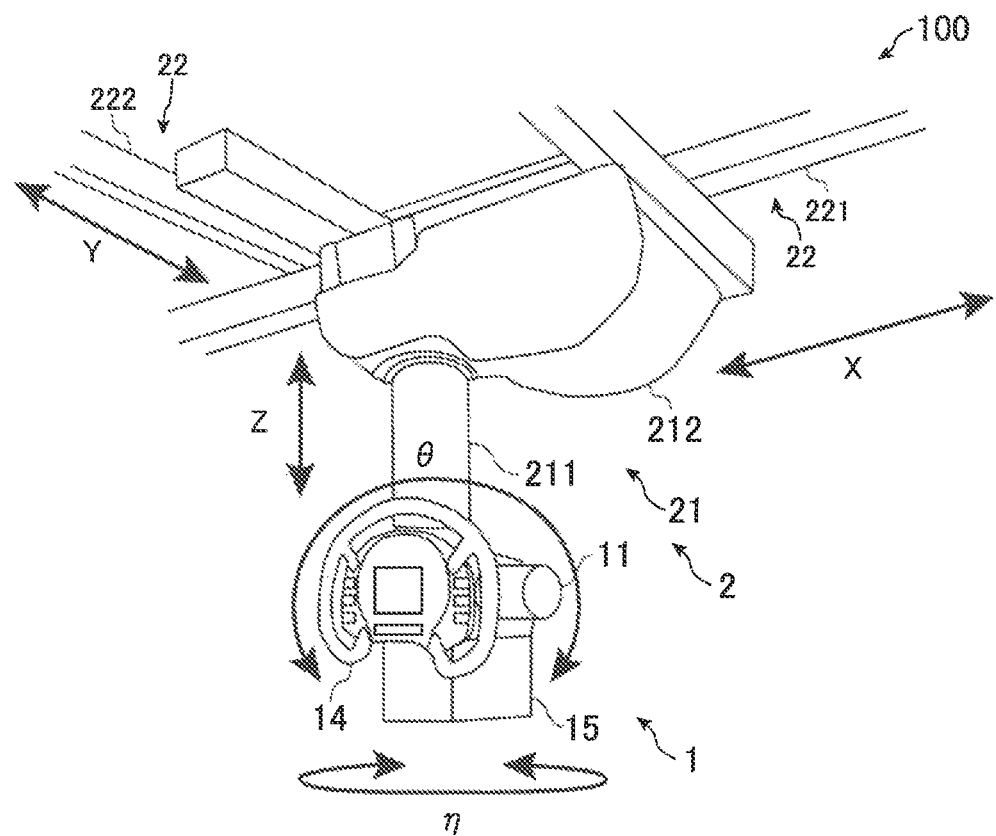
FIG. 3 is a diagram showing the configuration of a moving body and a moving mechanism of the X-ray imaging apparatus according to the embodiment of the present invention.
Figure 4:
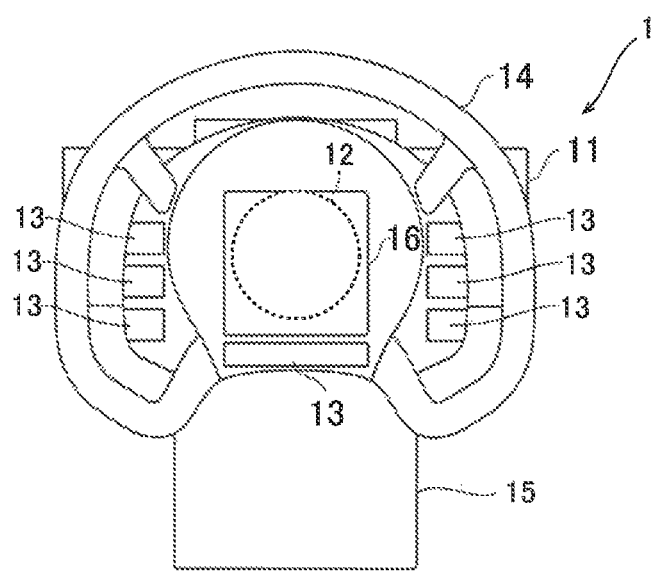
FIG. 4 is a diagram showing the configuration of the moving body of the X-ray imaging apparatus according to the embodiment of the present invention.

As shown in FIGS. 2 to 4, the moving body 1 includes the X-ray tube 11, a force sensor 12, a plurality of buttons 13, a grip 14, a collimator 15, and a touch panel 16. The force sensor 12 is an example of an "operating force detector" in the claims. The moving body 1 is configured to be movable in a plurality of directions (predetermined directions) by manual movement or control (described below) by the controller 3.

The X-ray tube 11 generates X-rays when a high voltage is applied thereto from a power source (not shown), and irradiates the subject 200 with the X-rays.

The force sensor 12 is disposed in the moving body 1 and can detect a force and a moment applied to the moving body 1 in each direction. Thus, the force sensor 12 functions as an operating force detector that detects an operating force applied to the moving body 1.

Specifically, the force sensor 12 is configured to detect a force in each of horizontal and vertical translational directions (X, Y, and Z directions) applied in order for an operator to manually move the moving body 1. In addition, the force sensor 12 is configured to detect a moment in each of rotational directions (θ and η directions) about a horizontal axis (R-axis) and a vertical axis (Z-axis) applied to the moving body 1. The force sensor 12 can detect detection direction components of the applied force and moment, and can measure the directions of the force and the moment and the magnitudes of the force and the moment. The detection results of the force sensor 12 are acquired by the controller 3.

The buttons 13 are a plurality of physical buttons disposed on the moving body 1 and pressed by the operator in order to perform the movement availability switching control (described below), and the plurality of buttons 13 are provided in the vicinity (on the grip 14 or near the grip 14) of the grip 14 of the moving body 1.

The grip 14 is provided on the moving body 1. The grip 14 is held by the operator when the operator manually moves the moving body 1, and transmits an operating force of the operator to the moving body 1.

The collimator 15 includes a plurality of shielding plates (collimator leaves), the positions of which can be adjusted, and has a function of adjusting an X-ray field by partially shielding the X-rays from the X-ray tube 11.

The touch panel 16 is configured to display imaging conditions and a method for X-ray imaging, and can receive input operations from the operator.

(Moving Mechanism)

As shown in FIGS. 1 and 3, the moving mechanism 2 includes a moving body support 21 that supports the moving body 1 in such a manner that the moving body 1 is movable in the plurality of directions (predetermined directions), and the guide 22 including a plurality of rails.

The moving body 1 can be moved by the moving mechanism 2 (the moving body support 21 and the guide 22) in the plurality of directions. As shown in FIGS. 1 and 3, a vertical (perpendicular) direction is defined as a Z direction, and two directions orthogonal to each other in the horizontal direction are defined as an X direction and a Y direction.

This embodiment shows an example in which the plurality of directions in which the moving body 1 can be moved by the moving mechanism 2 (the moving body support 21 and the guide 22) include a total of five directions including three translational directions (X, Y, and Z directions), a rotational direction (η direction) about the Z-axis in the vertical direction, and a rotational direction (θ direction) about the R-axis in the horizontal direction, as shown in FIG. 3.

As shown in FIG. 1, the moving body support 21 includes a rotary holder 213, a support rod 211, and a base 212. As shown in FIG. 2, motors 5 are provided inside the moving mechanism 2 (moving body support 21).

The motors 5 are servomotors that can switch between a torque control mode in which the torques of the motors 5 are controlled so as to change the amount of assist to be provided to the moving body 1 and a position control mode in which the motors 5 are controlled based on the current position and the movement target position of the moving body 1 to move the moving body 1, and are provided corresponding to respective axes.

As shown in FIG. 1, the support rod 211 holds the moving body 1 in such a manner that the moving body 1 can be translated in the vertical direction. The support rod 211 is suspended from the base 212 attached to the guide 22, and is expandable and contractable in the Z direction (vertical direction). With these configurations, the moving body support 21 supports the moving body 1 in such a manner that the moving body 1 is movable in the three translational directions (X, Y, and Z directions). In addition, the rotary holder 213 is provided at the tip (lower end) of the support rod 211.

The rotary holder 213 is supported by the support rod 211 so as to be rotatable in the η direction about the vertical axis (Z-axis). The Z-axis coincides with the central axis of the support rod 211. One end side of the rotary holder 213 is connected to the support rod 211 and holds the moving body 1 in such a manner that the moving body 1 is rotatable in the θ direction about the horizontal axis (R-axis). The R-axis is the radial direction (horizontal direction) of the support rod 211. With these configurations, the moving body support 21 supports the moving body 1 in such a manner that the moving body 1 is movable in the two rotational directions (η and θ directions).

The rotary holder 213 moves integrally with the moving body 1 in the plurality of directions (X, Y, Z, η, and θ), and thus the operator can move the moving body 1 in the plurality of directions (X, Y, Z, η, and θ) by holding the grip 14 and applying a force.

Figure 5:
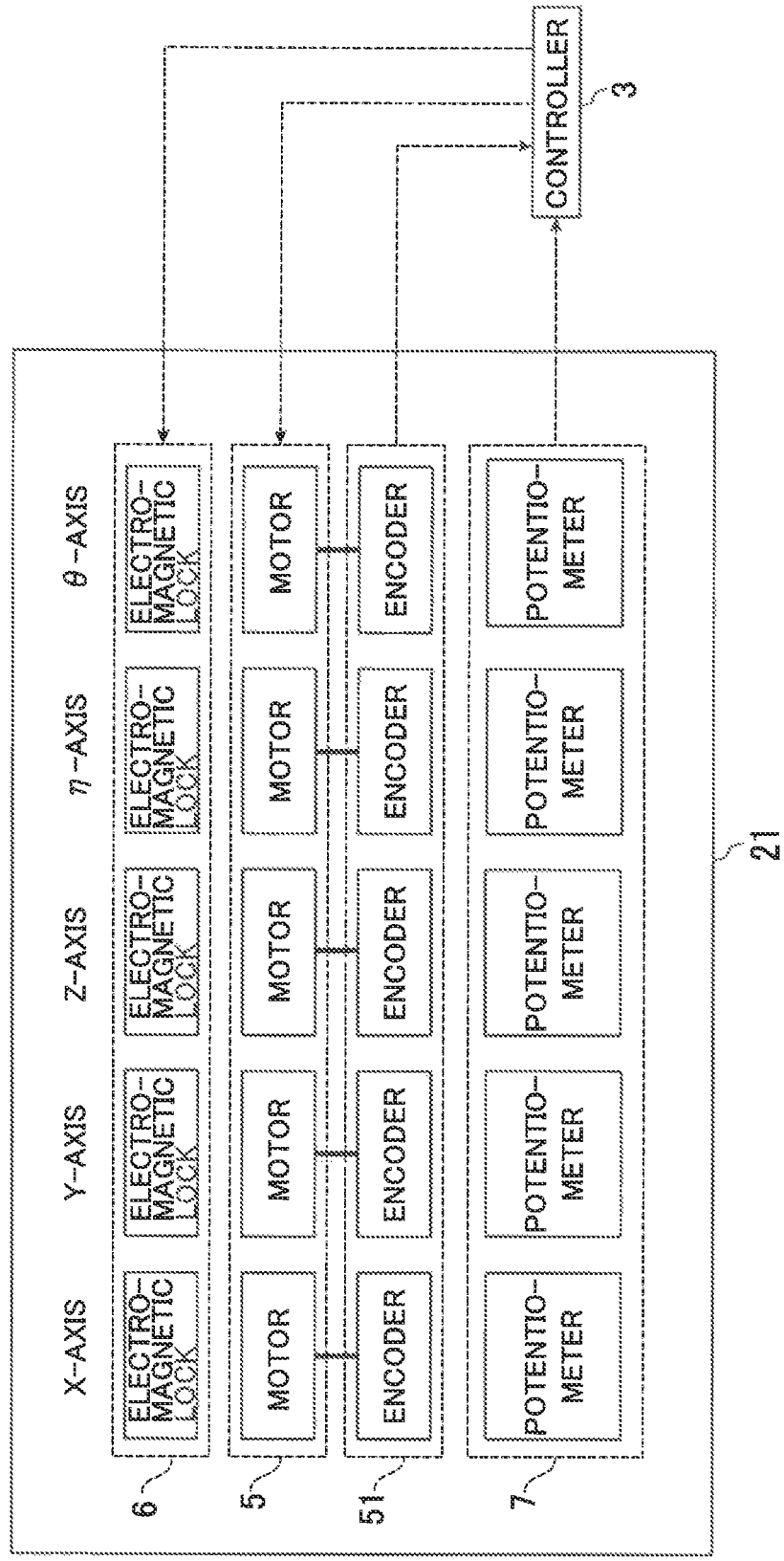
FIG. 5 is a block diagram showing the internal configuration of a moving body support and connection to a controller of the X-ray imaging apparatus according to the embodiment of the present invention.

As shown in FIG. 5, the moving body support 21 includes encoders 51 provided in the motors 5 for the respective axes, a movement availability switch 6, and a position detector 7.

The encoders 51 respectively detect the relative position of the moving body 1 in axial directions. Based on output signals of the encoders 51, it is possible to obtain the current position (the positions in the X, Y, and Z directions and the rotation angles in the η and θ directions) of the X-ray tube 11 of the moving body 1. The output signals of the encoders 51 are sent to the controller 3, and are used as positional information to control movement of the moving body 1.

The movement availability switch 6 switches between a state in which movement of the moving body 1 is permitted and a state in which the movement is prohibited in each of the plurality of directions under control of the controller 3.

The position detector 7 includes potentiometers provided for the respective axes. Furthermore, the position detector 7 detects the absolute position of the moving body 1 by electrically outputting the length of a wire that has been pulled out by movement of the moving body 1. The output signals of the potentiometers are sent to the controller 3, and are used as positional information to control movement of the moving body 1.

The guide 22 is provided on the ceiling of the imaging room 101, as shown in FIG. 1. The guide 22 includes the plurality of rails and supports the moving body support 21 in such a manner that the moving body support 21 can be translated in the X direction and the Y direction. With these configurations, the moving body support 21 supports the moving body 1 in such a manner that the moving body 1 is movable in the X direction and the Y direction (horizontal direction) along the guide 22.

Specifically, as shown in FIG. 3, the guide 22 includes a fixed rail 221 fixed to the ceiling surface and movable rails 222. The fixed rail 221 extends linearly in the X direction. The movable rails 222 are attached to the fixed rail 221 in such a manner as to be movable in the X direction. The movable rails 222 extend linearly in the Y direction. The base 212 of the support rod 211 is attached to the movable rails 222 in such a manner as to be movable in the Y direction.

(Assisting Means)

Assisting means configured to provide assist when the moving body 1 is manually moved is now described with reference to FIG. 5.

The moving body support 21 (base 212) includes a motor 5 for an X-axis and a transmission mechanism for the X-axis (not shown). The transmission mechanism for the X-axis includes a belt-pulley mechanism, for example. When the motor 5 for the X-axis is driven to rotate, an assisting force is applied in the X direction to a pair of movable rails 222 (moving body 1).

The moving body support 21 (base 212) includes a motor 5 for a Y-axis and a transmission mechanism for the Y-axis (not shown). The transmission mechanism for the Y-axis includes a belt-pulley mechanism, for example, similarly to the transmission mechanism for the X-axis. When the motor 5 for the Y-axis is driven to rotate, an assisting force is applied in the Y direction to the support rod 211 (moving body 1).

The moving body support 21 (base 212) includes a motor 5 for the Z-axis and a transmission mechanism for he Z-axis (not shown). The transmission mechanism for the Z-axis is a winding mechanism including a wire (not shown) connected to the rotary holder 213 at the lower end of the support rod 211, for example. When the motor 5 for the Z-axis is driven to wind up the wire, an assisting force is applied in the Z direction to the rotary holder 213 (moving body 1).

The moving body support 21 (support rod 211) includes a motor 5 for a η-axis that rotationally drives the rotary holder 213 about the Z-axis. It is not necessary to directly connect the motor 5 for the η-axis to the rotary holder 213, and a reduction gear or the like may be provided. The motor 5 for the η-axis applies an assisting force in the η direction to the rotary holder 213 (moving body 1).

The moving body support 21 (support rod 211) includes a motor 5 for a θ-axis that rotationally drives the moving body 1 about the R-axis. It is not necessary to directly connect the motor 5 for the θ-axis to the moving body 1, and a reduction gear or the like may be provided. The motor 5 for the θ-axis applies an assisting force in the θ direction to the moving body 1.

The encoders 51 are respectively connected to the motors (for the X-axis, Y-axis, Z-axis, η-axis, and θ-axis). The operation of each of the motors (for the X-axis, Y-axis, Z-axis, η-axis, and θ-axis) is controlled by the controller 3.

The controller 3 is configured to apply an assisting force in the moving direction of the moving body 1 to the moving body 1 based on the operating force detected by the force sensor 12. The controller 3 individually controls the motor 5 (for the X-axis, Y-axis, Z-axis, η-axis, or θ-axis) corresponding to a direction in which an assisting force is applied to be driven so as to generate an assisting force in the moving direction of the moving body 1.

(Movement Availability Switch)

As shown in FIG. 5, the movement availability switch 6 is provided inside the moving body support 21. The movement availability switch 6 includes a plurality of locking mechanisms that respectively lock movement of the moving mechanism 2 (moving body 1) corresponding to the plurality of directions.

Specifically, a plurality of electromagnetic locks (electromagnetic brakes) are provided as the locking mechanisms. As the locking mechanisms, hydraulic or mechanical brakes may be provided, for example. The electromagnetic locks are configured to releasably lock movement of the moving body 1 in the plurality of directions, respectively.

The electromagnetic locks are respectively provided for the plurality of directions including the X, Y, Z, η, and θ directions. The electromagnetic locks can switch between locking and unlocking in the X, Y, Z, η, and θ directions, respectively. Thus, the movement availability switch 6 can switch between the unlocked state (a state of permitting the movement) of the moving body 1 in each of the plurality of directions and the locked state (a state of prohibiting the movement) of the moving body 1 in each of the plurality of directions.

The movement availability switch 6 is constantly maintained in the state of prohibiting movement of the moving body 1 in each of the plurality of directions. Then, the movement availability switch 6 is individually switched to the state of permitting movement of the moving body 1 in a direction determined by the controller 3. The operation of each electromagnetic lock is controlled by the controller 3.

Switching between the locked state and the unlocked state is performed by input operations of the buttons 13. The moving body 1 is provided with the plurality of buttons 13 (unlock buttons) for respectively switching between the locked state and the unlocked state in the plurality of directions (X, Y, Z, η, and θ).

The controller 3 can perform control to determine a direction in which movement of the moving body 1 is permitted based on the input operation of each button 13. The controller 3 is configured to perform control to individually switch the direction in which the movement is permitted based on a direction corresponding to the button 13 on which the input operation has been performed.

A multiple direction release mode in which the plurality of electromagnetic locks are unlocked and movement of the moving body 1 in the plurality of directions is permitted and a free mode in which movement of the moving body 1 in all directions is permitted may be provided. In such a case, on the moving body 1, a multiple direction release mode button (not shown) and a free mode button (not shown) may be separately provided as mode switching buttons.

When receiving an input operation of the multiple direction release mode button (or the free mode button), the controller 3 starts control to switch the plurality of electromagnetic locks (or all electromagnetic locks) to an unlocking state. In this case, the operator holds the grip 14 and can freely move the moving body 1 in the plurality of direction (or all the directions).

When starting to control the multiple direction release mode (or the free mode), the controller 3 switches the electromagnetic locks to a state of prohibiting the movement in the plurality of directions based on a setting cancellation operation of the operator or a passage of time after permission of the movement in the plurality of directions. The setting cancellation operation of the operator includes inputting the multiple direction release mode button (or the free mode button) once to switch to the multiple direction release mode (or the free mode) and then inputting the multiple direction release mode button (or the free mode button) again, and inputting a dedicated cancel button (not shown), for example.

(Torque Control Mode)

The torque control mode is used when the moving body 1 is manually moved, and power assist control is performed based on the operating force. In the torque control mode, the controller 3 controls the torques of the motors 5 so as to change the amount of assist to be provided to the moving body 1. Under control of the controller 3, the motors 5 apply assisting forces corresponding to the magnitude of the force detected by the force sensor 12 (operating force detector) to the moving body 1. Specifically, when the operator holds the grip 14 and applies a force in the moving direction to move the moving body 1 in the torque control mode, the controller 3 controls the force sensor 12 (operating force detector) to detect the operating force. Furthermore, the controller 3 corrects the influence of the weight and pose of the moving body 1 on the detected operating force to convert the detected operating force into operating forces in the respective directions. Then, the controller 3 controls the torques of the motors 5 provided for the respective axes in the moving body support 21 so as to generate assisting forces obtained by multiplying the converted operating forces by assist ratios, as in an expression (1):

$$Ma = f_h - F_r + \alpha f_h \tag{1}$$

where M represents the mass of a moving portion (the moving body 1 and portions of the moving mechanism 2 moving when the moving mechanism 2 moves along the respective axes), a represents an acceleration, $f_h$ represents an operating force applied to the moving body 1, $F_r$ represents a resistance force, and α represents a ratio of the amount of assist to the operating force. M is several hundred kilograms, for example. In addition, α is about 2 or more and 10 or less, for example. That is, the operator's operation is assisted by a force of two to ten times the operating force. In this manner, the torques of the motors 5 are controlled so as to change the amount of assist to be provided to the moving body 1, and the moving body 1 (moving body support 21) is moved in the X, Y, and Z directions (the vertical direction and the horizontal direction) and the η and θ directions.

(Position Control Mode)

The position control mode is used for the auto positioning control, for example. In the position control mode, the controller 3 controls the motors 5 based on the current position and the movement target position of the moving body 1 to move the moving body 1. The absolute position (current position) of the moving body 1 in each axial direction is detected by the position detector 7 (potentiometer) provided for each axis. Furthermore, as necessary, the encoder 51 provided for each axis refers to the relative distance during the movement. The controller 3 controls the rotation speed of the motor 5 provided for each axis in the moving body support 21 so as to perform control of the moving speed. In this manner, the motors 5 are controlled based on the current position and the movement target position of the moving body 1 to move the moving body 1 in the X, Y, and Z directions (the vertical direction and the horizontal direction) and the η and θ directions, and the moving body support 21 is moved. Thus, in the auto positioning control, the moving body 1 can be automatically moved at a speed specified by the controller 3 based on the current position of the moving body 1 detected by the position detector 7 and the registered movement target position of the moving body 1. Note that an instruction to start the auto positioning control is given by an input operation through the remote control 4 or the like.

(Mode Switching Control)

The mode switching control performed by the controller 3 of this embodiment is now described based on a flowchart with reference to FIG. 6.

In step 301, the controller 3 determines whether or not the unlock button (button 13) has been pressed. The controller 3 detects whether or not the unlock button has been pressed as the presence or absence of an operation to enable manual movement of the moving body 1, and determines whether or not the control mode is switched to the torque control mode or the position control mode. When the unlock button has been pressed, the controller 3 advances to step 302. When the unlock button has not been pressed, the controller 3 advances to step 304.

In step 302, the controller 3 switches the control mode to the torque control mode, and advances to step 303. The controller 3 completes switching to the torque control mode by sending control signals to the motors 5 (servomotors) and switching the control mode of the motors 5 (servomotors) to the torque control mode in which the torques of the motors 5 are controlled so as to change the amount of assist to be provided to the moving body 1.

In step 303, the controller 3 executes power assist control, returns to step 301, and repeats the processing.

In step 304, the controller 3 switches the control mode to the position control mode, and advances to step 305. The controller 3 completes switching to the position control mode by sending control signals to the motors 5 (servomotors) and switching the control mode of the motors 5 (servomotors) to the position control mode in which the motors 5 are controlled based on the current position and the movement target position of the moving body 1 to move the moving body 1.

In step 305, the controller 3 determines whether or not a remote control operation has been performed. When the operation has been performed through the remote control 4, the controller 4 advances to step 306. When no operation has been performed through the remote control 4, the controller 3 returns to step 301, and repeats the processing.

In step 306, the controller 3 executes the auto positioning control. When completing the auto positioning control, the controller 3 returns to step 301, and repeats the processing.

The above processing is repeated such that the control operation of the mode switching control in which the control mode is switched is realized when the operation to enable manual movement of the moving body 1 is detected. When no operation is performed (when the unlock button is not pressed or the remote control 4 is not operated), the controller 3 keeps the control mode in a state in which it has been switched to the position control mode.

Advantages of this Embodiment

According to this embodiment, the following advantages are obtained.

According to this embodiment, as described above, the X-ray imaging apparatus 100 includes the controller 3 configured or programmed to perform the mode switching control to switch, based on whether or not the operation to enable manual movement of the moving body 1 has been detected, the control mode to the torque control mode in which the torques of the motors 5 are controlled so as to change the amount of assist to be provided to the moving body 1 when the moving body 1 is manually moved, or the position control mode in which the motors 5 are controlled based on the current position and the movement target position of the moving body 1 to move the moving body 1. Accordingly, when the X-ray tube 11 is manually moved, the control mode is switched to the torque control mode to control the generated torques of the motors 5 such that the operating force applied to move the moving body 1 can be assisted by controlling the torques (drive forces) of the motors 5. Therefore, the operating force is assisted by direct forces (torques), and thus it is possible to perform good power assist with no sense of strangeness. Consequently, it is possible to significantly reduce or prevent a decrease in operability when the X-ray tube 11 is manually moved. Furthermore, it is possible to switch the control mode to the position control mode in which high-precision position control is possible at the time of the auto positioning control in which the moving body 1 is automatically moved based on the current position and the registered movement target position of the moving body 1. Consequently, at the time of the auto positioning control, the high-precision position control can be performed. Thus, it is possible to accurately move the X-ray tube 11 when the X-ray tube 11 is automatically moved, and it is possible to significantly reduce or prevent a decrease in operability when the X-ray tube 11 is manually moved. Moreover, the controller 3 performs the mode switching control based on whether or not the operation to enable manual movement of the moving body 1 has been detected, and thus the controller 3 performs the mode switching control depending on whether or not the operator has performed the operation to enable manual movement of the moving body 1. Thus, when the operator manually moves the moving body 1, the control mode can be reliably switched to the torque control mode. Consequently, the control mode can be easily switched.

According to this embodiment, the X-ray imaging apparatus 100 further includes the movement availability switch 6 configured to switch between a state in which movement of the moving body 1 is permitted and a state in which the movement is prohibited in the predetermined directions (X, Y, Z, η, and θ directions), and the controller 3 is configured or programmed to perform the mode switching control based on detection of the switching operation of the movement availability switch 6 as whether or not the operation to enable manual movement of the moving body 1 has been detected. Accordingly, an operation of switching to a state in which the movement is permitted is performed such that the control mode can also be switched to the torque control mode. Furthermore, an operation of switching to a state in which the movement is prohibited is performed such that the control mode can also be switched to the position control mode. Consequently, it is possible to significantly reduce or prevent an increase in imaging procedures (the workload on the operator) as compared with the case in which an operation for switching the control mode is performed separately.

According to this embodiment, the X-ray imaging apparatus 100 further includes the grip 14 provided on the moving body 1 and held when the moving body 1 is manually moved and the plurality of buttons 13 provided in the vicinity of the grip 14, and the controller 3 is configured or programmed to switch the movement availability switch 6 and perform the mode switching control to switch the control mode to the torque control mode when at least one of the buttons 13 is pressed, and to switch the movement availability switch 6 and perform the mode switching control to switch the control mode to the position control mode when at least one of the pressed buttons 13 is released. Accordingly, as compared with the case in which a separate button 13 is provided to switch the control mode, it is possible to significantly reduce or prevent an increase in the number of components and to significantly reduce or prevent the complicated apparatus configuration.

According to this embodiment, the controller 3 is configured or programmed to perform the mode switching control based on whether or not the operating force detector (force sensor 12) has detected the operating force as whether or not the operation to enable manual movement of the moving body 1 has been detected. Accordingly, the control mode can be switched simply by manually moving the moving body 1, and thus unlike the case in which a separate button 13 is provided to switch the control mode, it is possible to significantly reduce or prevent an increase in the number of components and to significantly reduce or prevent the complicated apparatus configuration.

According to this embodiment, the moving mechanism 2 includes the guide 22 including the plurality of rails, and the moving body support 21 configured to support the moving body 1 in such a manner that the moving body 1 is movable in the vertical direction and the horizontal direction along the guide 22, and the controller 3 is configured or programmed to control the torques of the motors 5 so as to change the amount of assist to be provided to the moving body 1, and move the moving body support 21 in the vertical direction and the horizontal direction in the torque control mode, and to control the motors 5 based on the current position and the movement target position of the moving body 1 to move the moving body 1 in the vertical direction and the horizontal direction, and move the moving body support 21 in the position control mode. Accordingly, the moving body support 21 supporting the moving body 1 moves along the rails of the guide 22, and thus the moving body 1 and the moving body support 21 can be stably moved. Furthermore, even when the moving body 1 and the moving body support 21 are heavy, the moving body 1 and the moving body support 21 can be moved along the rails of the guide 22, and thus the moving body 1 and the moving body support 21 can be easily moved when the moving body 1 is manually moved.

According to this embodiment, the X-ray imaging apparatus 100 further includes the input device (remote control 4) through which the operation related to movement of the moving body 1 is performed, and the controller 3 is configured or programmed to perform the auto positioning control to automatically move the moving body 1 to the registered position based on the operation through the input device (remote control 4) in the position control mode. Accordingly, the auto positioning control can be performed in a state in which the control mode is switched to the position control mode in which the high-precision position control is possible, and thus the operator can easily and accurately move the moving body 1 to the target position.

According to this embodiment, the motors 5 include servomotors configured to switch between the torque control mode in which the torques of the motors 5 are controlled so as to change the amount of assist to be provided to the moving body 1 and the position control mode in which the motors 5 are controlled based on the current position and the movement target position of the moving body 1 to move the moving body 1, and the controller 3 is configured or programmed to switch the motors 5 (servomotors) to the torque control mode or the position control mode based on whether or not the operation to enable manual movement of the moving body 1 has been detected. Accordingly, the torque control mode and the position control mode can be driven by the common motors 5 (servo motors), and thus as compared with the case in which the motors 5 are provided separately for each of the torque control mode and the position control mode, it is possible to significantly reduce or prevent an increase in the number of components and to significantly reduce or prevent the complicated apparatus configuration.

MODIFIED EXAMPLES

The embodiment disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

For example, while the X-ray imaging apparatus 100 of the present invention is a ceiling-suspended X-ray imaging apparatus in the aforementioned embodiment, the present invention is not limited to this. That is, the present invention may alternatively be applied to a C-arm type X-ray imaging apparatus, or an X-ray imaging apparatus in which an X-ray detector is manually moved as in a proximate fluoroscopic table.

While the X-ray tube 11 is provided on the moving body 1 in the aforementioned embodiment, the present invention is not limited to this. In the present invention, the X-ray detector may alternatively be provided on the moving body.

While the buttons 13 are physical buttons in the aforementioned embodiment, the present invention is not limited to this. In the present invention, the buttons may alternatively be buttons displayed on the touch panel.

While the controller 3 is disposed (provided) outside the imaging room 101 in the aforementioned embodiment, the present invention is not limited to this. In the present invention, the controller may alternatively be disposed inside the imaging room, or may alternatively be built in the moving body or the moving mechanism.

While the input device is the remote control 4 in the aforementioned embodiment, the present invention is not limited to this. In the present invention, the input device may alternatively be an input device such as a mouse or a keyboard.

While the common motors 5 (servomotors) are driven in both the torque control mode and the position control mode in the aforementioned embodiment, the present invention is not limited to this. In the present invention, different motors may alternatively be driven by switching between the torque control mode and the position control mode.

While the auto positioning control is performed in the position control mode in the aforementioned embodiment, the present invention is not limited to this. In the present invention, long image capturing and tomographic imaging may alternatively be performed in the position control mode, for example.

While the controller 3 takes the presence or absence of the switching operation of the movement availability switch 6 as the presence or absence of an operation for performing the mode switching control (operation of manually moving the moving body 1) in the aforementioned embodiment, the present invention is not limited to this. In the present invention, the controller may alternatively perform the mode switching control, taking the presence or absence of an operating force detected by the force sensor as the presence or absence of the operation for performing the mode switching control.

While the position detector 7 includes the potentiometers in the aforementioned embodiment, the present invention is not limited to this. In the present invention, the position detector may alternatively include encoders or laser distance measurement sensors, for example.

While the processing operations of the controller 3 are described using a flowchart in a flow-driven manner in which the processing operations are performed in order along a processing flow for the convenience of illustration in the aforementioned embodiment, the present invention is not limited to this. In the present invention, the processing operations of the controller may alternatively be performed in an event-driven manner in which the processing operations are performed on an event basis. In this case, the processing operations may be performed in a complete event-driven manner or in a combination of an event-driven manner and a flow-driven manner.

What is claimed is:

1. An X-ray imaging apparatus comprising:
   an X-ray tube configured to irradiate a subject with X-rays;
   an X-ray detector configured to detect the X-rays transmitted through the subject;
   a moving body including at least one of the X-ray tube and the X-ray detector, the moving body being movable in a predetermined direction;
   a moving mechanism configured to support the moving body in such a manner that the moving body is movable in the predetermined direction;
   a motor provided in the moving mechanism;
   an operating force detector configured to detect an operating force applied to move the moving body;
   a controller configured or programmed to perform mode switching control to switch, based on whether or not an operation to enable manual movement of the moving body has been detected, a control mode to a torque control mode in which a torque of the motor is controlled so as to change an amount of assist to be provided to the moving body when the moving body is manually moved, or a position control mode in which the motor is controlled to move the moving body based on a current position and a movement target position of the moving body; and
   a common switching button commonly used for switching between the torque control mode and the position control mode concurrently and switching a movement state of the moving body between a locked state and an unlocked state.

2. The X-ray imaging apparatus according to claim 1, further comprising a movement availability switch configured to switch between a state in which movement of the moving body is permitted in the predetermined direction and a state in which the movement is prohibited in the predetermined direction; wherein
   the controller is configured or programmed to perform the mode switching control based on detection of a switching operation of the movement availability switch as whether or not the operation to enable the manual movement of the moving body has been detected.

3. The X-ray imaging apparatus according to claim 2, further comprising:
   a grip provided on the moving body and held when the moving body is manually moved; wherein
   the common switching button is provided in a vicinity of the grip, and
   the controller is configured or programmed to switch to the unlocked state and perform the mode switching control to switch the control mode to the torque control mode when the common switching button is pressed, and to switch to the locked state and perform the mode switching control to switch the control mode to the position control mode when the common switching button that has been pressed is released.

4. The X-ray imaging apparatus according to claim 1, wherein the controller is configured or programmed to perform the mode switching control based on whether or not the operating force detector has detected the operating force as whether or not the operation to enable the manual movement of the moving body has been detected.

5. The X-ray imaging apparatus according to claim 1, wherein
   the moving mechanism includes a guide including a plurality of rails, and a moving body support configured to support the moving body in such a manner that the moving body is movable in a vertical direction and a horizontal direction along the guide; and
   the controller is configured or programmed to control the torque of the motor so as to change the amount of assist to be provided to the moving body, and move the moving body support in the vertical direction and the horizontal direction in the torque control mode, and to control the motor based on the current position and the movement target position of the moving body to move the moving body in the vertical direction and the horizontal direction, and move the moving body support in the position control mode.

6. The X-ray imaging apparatus according to claim 1, further comprising an input device through which an operation related to movement of the moving body is performed; wherein
   the controller is configured or programmed to perform auto positioning control to automatically move the moving body to a registered position based on the operation through the input device in the position control mode.

7. The X-ray imaging apparatus according to claim 1, wherein
   the motor includes a servomotor configured to switch between the torque control mode in which the torque of the motor is controlled so as to change the amount of assist to be provided to the moving body and the position control mode in which the motor is controlled based on the current position and the movement target position of the moving body to move the moving body; and the controller is configured or programmed to switch the motor to the torque control mode or the position control mode based on whether or not the operation to enable the manual movement of the moving body has been detected.

* * * * *